(12) United States Patent
Yamane et al.

(10) Patent No.: US 9,771,384 B2
(45) Date of Patent: Sep. 26, 2017

(54) FLUOROCHEMICAL SURFACE TREATING AGENT AND ARTICLE TREATED THEREWITH

(71) Applicant: Shin-Etsu Chemical Co., Ltd., Tokyo (JP)

(72) Inventors: Yuji Yamane, Annaka (JP); Takashi Matsuda, Annaka (JP); Ryusuke Sakoh, Annaka (JP); Noriyuki Koike, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 57 days.

(21) Appl. No.: 14/810,670

(22) Filed: Jul. 28, 2015

(65) Prior Publication Data

US 2016/0040039 A1    Feb. 11, 2016

(30) Foreign Application Priority Data

Aug. 7, 2014  (JP) ................. 2014-161004

(51) Int. Cl.
| | |
|---|---|
| C07F 7/00 | (2006.01) |
| C07F 7/08 | (2006.01) |
| C07F 7/18 | (2006.01) |
| C03C 17/30 | (2006.01) |
| B05D 1/18 | (2006.01) |
| C08G 65/336 | (2006.01) |

(52) U.S. Cl.
CPC ............ *C07F 7/1836* (2013.01); *C03C 17/30* (2013.01); *C07F 7/00* (2013.01); *C07F 7/0843* (2013.01); *C08G 65/336* (2013.01); *B05D 1/185* (2013.01); *C03C 2217/76* (2013.01)

(58) Field of Classification Search
CPC ........ C07F 7/0843; C07F 7/00; C07F 7/1836; C03C 2217/76; C03C 17/30; C08G 65/336; B05D 1/185
See application file for complete search history.

(56) References Cited

U.S. PATENT DOCUMENTS

| | | | |
|---|---|---|---|
| 7,196,212 B2 * | 3/2007 | Yamaguchi | C08G 65/007 |
| | | | 556/463 |
| 8,420,763 B2 * | 4/2013 | Yamane | C08G 65/007 |
| | | | 528/42 |
| 8,900,711 B2 | 12/2014 | Yamane et al. | |
| 2013/0108876 A1 * | 5/2013 | Komori | C03C 17/30 |
| | | | 428/421 |
| 2013/0220177 A1 * | 8/2013 | Iyer | C09D 4/00 |
| | | | 106/287.14 |
| 2013/0228100 A1 * | 9/2013 | Kleyer | C07F 7/14 |
| | | | 106/287.14 |
| 2014/0113145 A1 | 4/2014 | Yamane et al. | |
| 2014/0272725 A1 * | 9/2014 | Hamade | G03F 7/16 |
| | | | 430/325 |
| 2015/0210587 A1 * | 7/2015 | Gao | C03C 17/30 |
| | | | 428/429 |
| 2015/0307719 A1 | 10/2015 | Mitsuhashi et al. | |

FOREIGN PATENT DOCUMENTS

| | | | | |
|---|---|---|---|---|
| EP | 2 436 716 A1 | | 4/2012 | |
| EP | 2436716 A1 * | | 4/2012 | .......... C08G 65/007 |
| EP | 2 725 078 A1 | | 4/2014 | |
| JP | 2003-238577 | | 8/2003 | |
| JP | 2012-72272 | | 4/2012 | |
| JP | 2014-84405 | | 5/2014 | |
| WO | 2014/069592 A1 | | 5/2014 | |

OTHER PUBLICATIONS

Office Action dated Jun. 6, 2017 issued in corresponding Japanese patent application No. 2014-161004.

\* cited by examiner

*Primary Examiner* — Nicole M Buie-Hatcher
(74) *Attorney, Agent, or Firm* — Oblon, McClelland, Maier & Neustadt, L.L.P.

(57) ABSTRACT

A fluorochemical surface treating agent comprising a hydrolyzable group-containing silane modified with a fluorooxyalkylene-containing polymer and/or a partial hydrolytic condensate thereof forms a water/oil repellent layer having chemical resistance and mar resistance.

18 Claims, No Drawings

FLUOROCHEMICAL SURFACE TREATING AGENT AND ARTICLE TREATED THEREWITH

CROSS-REFERENCE TO RELATED APPLICATION

This non-provisional application claims priority under 35 U.S.C. §119(a) on Patent Application No. 2014-161004 filed in Japan on Aug. 7, 2014, the entire contents of which are hereby incorporated by reference.

TECHNICAL FIELD

This invention relates to a fluorochemical surface treating agent, more particularly to a fluorochemical surface treating agent comprising a hydrolyzable group-containing silane modified with a fluorooxyalkylene-containing polymer and/or a partial hydrolytic condensate thereof, capable of forming a coating having water/oil repellency and mar resistance, especially chemical resistance, and an article treated therewith.

BACKGROUND ART

For better appearance and visibility, there is recently an increasing need for the technology for tailoring the surface of optical articles to be fingerprint proof or easy in stain removal. In particular, since eyeglass lenses, wearable terminals, and touch panel displays are readily fouled with stains like sebum, it is desired to form a water/oil repellent layer on their surface. In the state-of-the-art, there are available surface treating agents having antifouling, stain wipe-off, abrasion resistance and mar resistance. However, they are insufficient in chemical resistance, leaving the problem that their performance is degraded with fingerprints and detergents with the lapse of time.

Generally, fluorooxyalkylene-containing compounds exhibit, by virtue of their extremely low surface free energy, water/oil repellency, chemical resistance, lubricity, parting, antifouling and other properties. Taking advantage of these properties, they find use in a variety of industrial fields as water/oil repellent antifouling agents for paper and textiles, lubricants for magnetic recording media, oil-repellent agents for precision instruments, parting agents, cosmetic ingredients, protective films and the like. Inversely, the same properties indicate non-tackiness or non-adhesion to other substrates. Even if they can be coated to the substrate surface, it is difficult for the coating to tightly adhere thereto.

On the other hand, silane coupling agents are well known for their ability to bond surfaces of glass or fabric substrates to organic compounds. They are widely used as surface coating agents for numerous substrates. The silane coupling agent contains an organic functional group and a reactive silyl group (typically hydrolyzable silyl) in the molecule. In the presence of airborne moisture or the like, the hydrolyzable silyl groups undergo self-condensation reaction to form a coating. As the hydrolyzable silyl groups form chemical and physical bonds with the surface of glass or fabric, the coating becomes a tough coating having durability.

Patent Document 1 discloses a fluorooxyalkylene group-containing silane represented by the following formula.

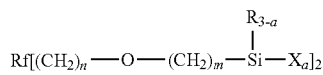

Herein Rf is a divalent linear perfluorooxyalkylene group, R is $C_1$-$C_4$ alkyl or phenyl, X is a hydrolyzable group, n is an integer of 0 to 2, m is an integer of 1 to 5, and a is 2 or 3. When treated with this fluorooxyalkylene-containing silane, glass and antireflective film are improved in stain wipe-off. However, since both terminal groups are bonded to the substrate, surface lubricity is insufficient, and the coating is less satisfactory in sliding and mar resistance.

CITATION LIST

Patent Document 1: JP-A 2003-238577
Patent Document 2: JP-A 2012-072272
(U.S. Pat. No. 8,900,712, EP 2436716)
Patent Document 3: JP-A 2014-084405
(US 20140113145, EP 2725078)

DISCLOSURE OF INVENTION

In Patent Document 2, the inventors proposed a fluorooxyalkylene-containing silane of the formula shown below. When glass is treated with the fluorooxyalkylene-containing silane, improvements in lubricity and mar resistance are available. However, this still fails to meet the requirements of mar resistance and chemical resistance which become severer in these days.

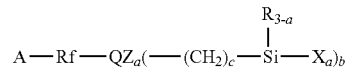

Herein Rf is —$(CF_2)_d$—$(OC_2F_4)_e(OCF_2)_f$—$O(CF_2)_d$—, A is a monovalent fluorinated group terminated with a —$CF_3$ group, Q is a divalent organic group, Z is a di- to octa-valent organopolysiloxane residue having a siloxane bond, R is $C_1$-$C_4$ alkyl or phenyl, X is a hydrolyzable group, a is 2 or 3, b is an integer of 1 to 6, c is an integer of 1 to 5, α is 0 or 1, d is independently an integer of 0 to 5, e is an integer of 0 to 80, f is an integer of 0 to 80, the sum e+f is an integer of 5 to 100, and the repeating units may be randomly arranged.

Also the inventors proposed a polymer composition in Patent Document 2 and a fluorooxyalkylene-containing silane of the formula shown below in Patent Document 3, both forming a chemical resistance film. They are still insufficient to meet both mar resistance and chemical resistance because the requirement of mar resistance becomes outstandingly severer in these days.

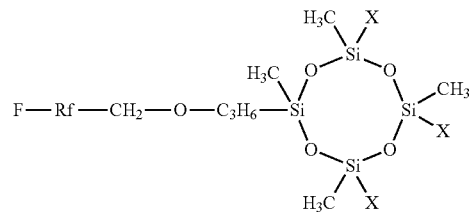

Herein Rf is a divalent perfluorooxyalkylene-containing group, X is —$(CH_2)_n$SiX' or hydrogen, one or less of X is hydrogen, n is an integer of 2 to 10, and X' is a hydrolyzable group.

While touch panel displays and wearable terminals are generally surface coated with water/oil repellent layers, it is desirable from the aspects of scratch resistance and fingerprint wipe-out that the water/oil repellent layers have a low coefficient of dynamic friction. In this regard, it is desired to develop a water/oil repellent layer having improved mar resistance and a low coefficient of dynamic friction. Since these terminals are intended for outdoor use as well, the layer is also required to be resistant to salt water, acid and alkali.

An object of the invention is to provide a fluorochemical surface treating agent comprising a hydrolyzable group-containing silane modified with a fluorooxyalkylene-containing polymer and/or a partial hydrolytic condensate thereof, capable of forming a water/oil repellent layer having significantly improved mar resistance as well as chemical resistance, and an article treated therewith.

The inventors have found that when forming a film, a polymer based on a fluorooxyalkylene structure backbone and having a hydrolyzable group at one end of its molecular chain imparts better mar resistance to the film than a polymer based on a fluorooxyalkylene structure backbone and having hydrolyzable groups at both ends of its molecular chain. It has been found that a fluorochemical surface treating agent comprising a polymer based on a fluorooxyalkylene structure backbone, having a siloxane bond-free linking group, and having a plurality of hydrolyzable groups forms a water/oil repellent layer having improved mar resistance and chemical resistance.

In one aspect, the invention provides a fluorochemical surface treating agent comprising (A) a hydrolyzable group-containing silane modified with a fluorooxyalkylene-containing polymer, represented by the average compositional formula (1) and/or a partial hydrolytic condensate thereof.

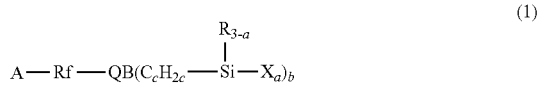

Herein A is a monovalent fluorinated group terminated with —$CF_3$; Rf is —$(CF_2)_d$—$(OCF_2)_p(OCF_2CF_2)_q$ $(OCF_2CF_2CF_2)_r$—$(OCF_2CF_2CF_2CF_2)_s(OCF(CF_3)CF_2)_t$—$O(CF_2)_d$—, d is independently an integer of 0 to 5, p, q, r, s and t are each independently an integer of 0 to 200, p+q+r+s+t is 10 to 200, units in parentheses may be randomly arranged; Q is a single bond or a divalent organic group; B is a divalent group: -$J_2C$—, a divalent group: -$L_2Si$—, a trivalent group: -JC≡, a trivalent group: -LSi≡, a tetravalent group: —C≡, or a tetravalent group: —Si≡, wherein J is independently an alkyl group, hydroxyl group or silyl ether group: $K_3SiO$—, K is independently hydrogen, alkyl, aryl or alkoxy, L is independently alkyl, alkoxy or chloro; R is a monovalent organic group; X is a hydrolyzable group, a is an integer of 1 to 3, b is an integer of 1 to 3, an average of b being 1.5 to 3.0, c is an integer of 1 to 10.

The surface treating agent may further comprise (B) a hydrolyzable group-containing silane modified with a fluorooxyalkylene-containing polymer, represented by the average compositional formula (2) and/or a partial hydrolytic condensate thereof, wherein component (B) is present in an amount of 0.1 to 20 mol % based on the total moles of components (A) and (B),

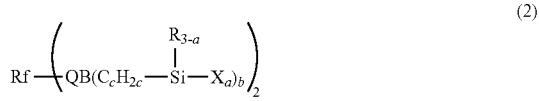

wherein Rf, Q, B, R, X, a, b, and c are as defined in formula (1).

The surface treating agent may further comprise (C) a fluorooxyalkylene-containing polymer having the general formula (3), wherein component (C) is present in an amount of 0.1 to 40 mol % based on the total moles of components (A), (B) and (C), provided that component (B) is optional.

wherein Rf is as defined in formula (1) and D is independently fluorine, hydrogen, or a monovalent fluorinated group terminated with —$CF_3$, —$CF_2H$ or —$CFH_2$.

In a preferred embodiment, Q is a single bond or a substituted or unsubstituted, divalent hydrocarbon group of 2 to 12 carbon atoms which may contain at least one structure selected from an amide bond, ether bond, ester bond, diorganosilylene group, and —Si[OH][$(CH_2)_g$Si$(CH_3)_3$]— wherein g is an integer of 2 to 4.

In a preferred embodiment, X is a hydrolyzable group selected from the group consisting of $C_1$-$C_{10}$ alkoxy groups, $C_2$-$C_{10}$ alkoxyalkoxy groups, $C_1$-$C_{10}$ acyloxy groups, $C_2$-$C_{10}$ alkenyloxy groups, halogen groups, and silazane groups.

Typically, the surface treating agent is diluted with a solvent. The solvent is preferably selected from among methyl perfluorobutyl ether, ethyl perfluorobutyl ether, methoxyperfluoroheptene, decafluoropentane, pentafluorobutane, and perfluorohexane.

Also contemplated herein is an article, specifically optical article, which is treated with the surface treating agent defined above. Typical of the article are glass, chemically strengthened glass, physically strengthened glass, $SiO_2$-deposited glass, sapphire glass, $SiO_2$-deposited sapphire glass, quartz substrate, and metal, which are treated with the surface treating agent defined above. Most preferred are a touch panel, antireflective film, wearable terminal, eyeglass lens, and solar cell panel which are treated with the surface treating agent defined above.

Advantageous Effects of Invention

A fluorochemical surface treating agent comprising a hydrolyzable group-containing silane modified with a fluorooxyalkylene-containing polymer and/or a partial hydrolytic condensate thereof forms a film having improved mar resistance and chemical resistance. When articles are treated with the surface treating agent, the articles are endowed with water/oil repellency, fingerprint wipe-out, mar resistance and chemical resistance. By virtue of mar resistance and chemical resistance, water/oil repellency lasts long.

DESCRIPTION OF PREFERRED EMBODIMENTS

The notation (Cn-Cm) means a group containing from n to m carbon atoms per group. Me stands for methyl.

The invention provides a fluorochemical surface treating agent comprising (A) a hydrolyzable group-containing silane modified with a fluorooxyalkylene-containing polymer, represented by the average compositional formula (1), referred to as "single end hydrolyzable polymer" hereinafter, and/or a partial hydrolytic condensate thereof, and preferably further comprising (B) a hydrolyzable group-contain ing silane modified with a fluorooxyalkylene-containing polymer, represented by the average compositional formula (2), referred to as "dual end hydrolyzable polymer" hereinafter, and/or a partial hydrolytic condensate thereof, or (C) a fluorooxyalkylene-containing polymer represented by the general formula (3), referred to as "nonfunctional polymer" hereinafter.

$$A—Rf—QB(C_cH_{2c}—\underset{R_{3-a}}{\underset{|}{Si}}—X_a)_b \quad (1)$$

$$Rf—\left(QB(C_cH_{2c}—\underset{R_{3-a}}{\underset{|}{Si}}—X_a)_b\right)_2 \quad (2)$$

$$D—Rf—D \quad (3)$$

Herein A is a monovalent fluorinated group terminated with $—CF_3$; Rf is $—(CF_2)_d—(OCF_2)_p(OCF_2CF_2)_q(OCF_2CF_2CF_2)_r—(OCF_2CF_2CF_2CF_2)_s(OCF(CF_3)CF_2)_t—O(CF_2)_d—$, d is independently an integer of 0 to 5, p, q, r, s and t are each independently an integer of 0 to 200, p+q+r+s+t is 10 to 200, units in parentheses may be randomly arranged; Q is a single bond or a divalent organic group; B is a divalent group: $-J_2C—$, a divalent group: $-L_2Si—$, a trivalent group: $-JC\equiv$, a trivalent group: $-LSi\equiv$, a tetravalent group: $—C\equiv$, or a tetravalent group: $—Si\equiv$, wherein J is independently an alkyl group, hydroxyl group or silyl ether group: $K_3SiO—$, K is independently hydrogen, alkyl, aryl or alkoxy, L is independently alkyl, alkoxy or chloro; R is a monovalent organic group; X is a hydrolyzable group, a is an integer of 1 to 3, b is an integer of 1 to 3, an average of b is 1.5 to 3.0, c is an integer of 1 to 10; D is independently fluorine, hydrogen, or a monovalent fluorinated group terminated with $—CF_3$, $—CF_2H$ or $—CFH_2$.

In formulae (1) to (3), Rf indicative of the backbone structure of fluorooxyalkylene-containing polymer is represented by $—(CF_2)_d—(OCF_2)_p(OCF_2CF_2)_q(OCF_2CF_2CF_2)_r—(OCF_2CF_2CF_2CF_2)_s(OCF(CF_3)CF_2)_t—O(CF_2)_d—$. Herein, d is independently an integer of 0 to 5, preferably 0 to 2, and more preferably 1 or 2; p, q, r, s and t are each independently an integer of 0 to 200, preferably p is an integer of 10 to 150, q is an integer of 10 to 150, r is an integer of 0 to 20, s is an integer of 0 to 20, t is an integer of 0 to 20, p+q+r+s+t is an integer of 10 to 200, preferably 20 to 150, and more preferably 30 to 100. Units in parentheses may be randomly arranged. If one of p, q, r, s and t exceeds 200, the fluorooxyalkylene group has too high a molecular weight, and the functionality equivalent of hydrolyzable silyl group is accordingly reduced, resulting in poor adhesion to the substrate and low reactivity on synthesis. If p+q+r+s+t exceeds the upper limit, chemical resistance is adversely affected. If p+q+r+s+t is below the lower limit, fingerprint wipe-out and abrasion resistant properties characteristic of fluorooxyalkylene are not fully exerted, that is, fingerprint wipe-out and abrasion resistance are adversely affected.

Illustrative examples of Rf are given below.

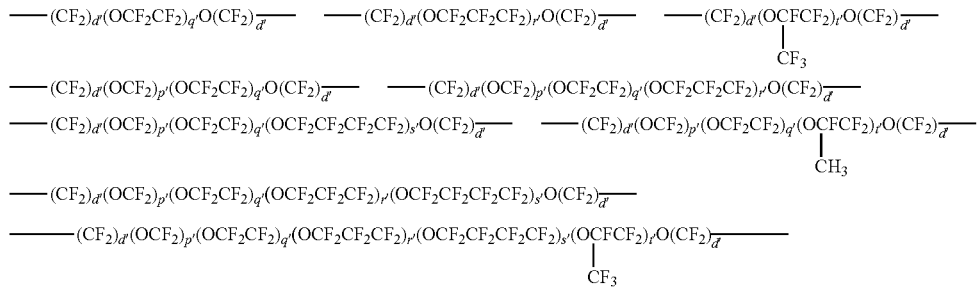

Herein d', p' and q' are as defined for d, p and q, respectively, r', s' and t' each are an integer of at least 1, with their upper limit being the same as r, s and t.

In formula (1), A is a monovalent fluorinated group terminated with $—CF_3$, preferably $C_1$-$C_6$ perfluoro group, and more preferably $—CF_3$ or $—CF_2CF_3$.

In formulae (1) and (2), Q is a single bond or divalent organic group. The single bond is a link between Rf group and B group. The divalent organic group is preferably an optionally substituted, divalent organic group of 2 to 12 carbon atoms, preferably optionally substituted, divalent hydrocarbon group of 2 to 12 carbon atoms, which may contain one or more structure selected from an amide bond, ether bond, ester bond, diorganosilylene group (e.g., dimethylsilylene, diethylsilylene and diphenylsilylene), and $—Si[OH][(CH_2)_gSi(CH_3)_3]—$ wherein g is an integer of 2 to 4.

Examples of the optionally substituted, divalent hydrocarbon group of 2 to 12 carbon atoms include alkylene groups such as ethylene, propylene (trimethylene, methylethylene), butylene (tetramethylene, methylpropylene), hexamethylene and octamethylene, arylene groups such as phenylene, and combinations of two or more thereof (e.g., alkylene-arylene), as well as substituted forms of the foregoing in which some or all hydrogen atoms are substituted by halogen atoms such as fluorine, chlorine, bromine and iodine. Inter alia, optionally substituted $C_2$-$C_4$ alkyl and phenyl groups are preferred.

Illustrative examples of Q are given below.

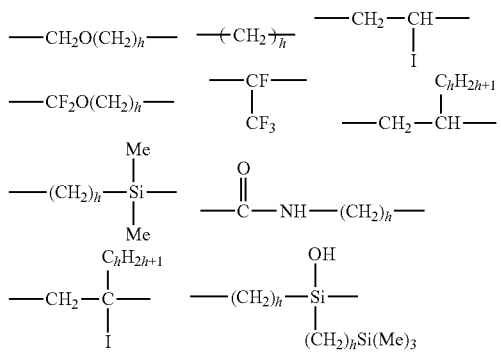

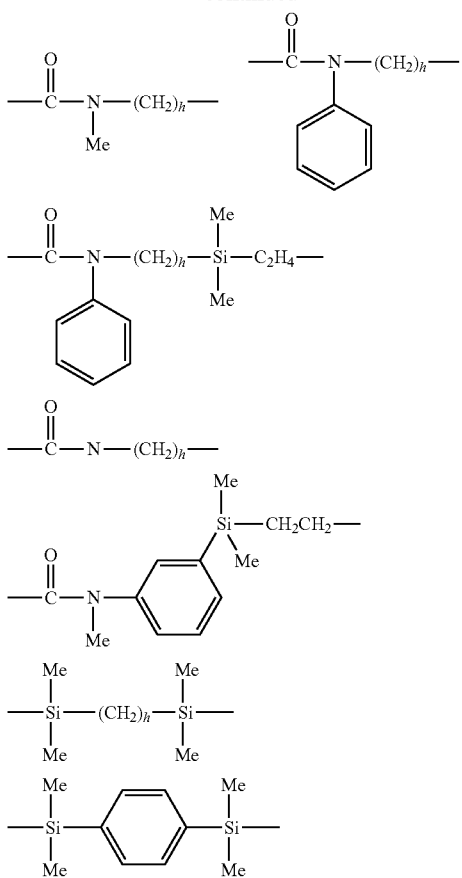
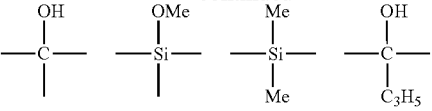

Herein h is an integer of 2 to 4.

In formulae (1) and (2), B is a divalent group: -J$_2$C—, a divalent group: -L$_2$Si—, a trivalent group: -JC=, a trivalent group: -LSi=, a tetravalent group: —C≡, or a tetravalent group: —Si≡. Herein J is independently alkyl, preferably C$_1$-C$_3$ alkyl, hydroxyl group or silyl ether group: K$_3$SiO—; K is independently hydrogen, alkyl, preferably C$_1$-C$_3$ alkyl, aryl such as phenyl, or alkoxy, preferably C$_1$-C$_3$ alkoxy; and L is independently alkyl, preferably C$_1$-C$_3$ alkyl, alkoxy, preferably C$_1$-C$_3$ alkoxy or chloro.

Illustrative examples of B are given below.

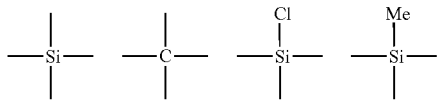
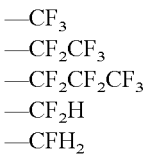

In formulae (1) and (2), X is each independently a hydrolyzable group. Suitable hydrolyzable groups include C$_1$-C$_{10}$ alkoxy groups such as methoxy, ethoxy, propoxy and butoxy, C$_2$-C$_{10}$ alkoxyalkoxy groups such as methoxymethoxy and methoxyethoxy, C$_1$-C$_{10}$ acyloxy groups such as acetoxy, C$_2$-C$_{10}$ alkenyloxy groups such as isopropenoxy, halogen groups such as chloro, bromo and iodo, and silazane groups. Inter alia, methoxy, ethoxy, isopropenoxy and chloro are preferred.

In formulae (1) and (2), R is a monovalent organic group, preferably a C$_1$-C$_4$ alkyl group such as methyl, ethyl, propyl or butyl, or a phenyl group. Most preferred is methyl.

The subscript a is an integer of 1 to 3, and preferably 2 or 3 for reactivity and substrate adhesion. The subscript b is an integer of 1 to 3, an average of b is 1.5 to 3.0, preferably 1.8 to 3.0. If an average of b is less than 1.5, chemical resistance is adversely affected. If an average of b exceeds 3.0, which means more hydrolyzable groups, there may arise problems including viscosity buildup, complicated preparation, low shelf stability, and low water/oil repellency due to a low content of non-fluorinated group. The subscript c is an integer of 1 to 10, preferably 3 to 8.

The single end hydrolyzable polymer of formula (1) has 1 to 9, preferably 4 to 9 hydrolyzable groups X. The dual end hydrolyzable polymer of formula (2) has 2 to 18, preferably 8 to 18 hydrolyzable groups X.

In formula (3), D is independently fluorine, hydrogen, or a monovalent fluorinated group terminated with —CF$_3$, —CF$_2$H or —CFH$_2$. Examples of the fluorinated group terminated with —CF$_3$, —CF$_2$H or —CFH$_2$ are given below.
—CF$_3$
—CF$_2$CF$_3$
—CF$_2$CF$_2$CF$_3$
—CF$_2$H
—CFH$_2$ Examples of the single end hydrolyzable polymer of formula (1) wherein linking group Q is —CH$_2$—O—C$_3$H$_6$—, B is —Si≡, and X is —OCH$_3$ are shown below. The combination of Q, B and X is not limited thereto, and a series of single end hydrolyzable polymers are available by merely changing Q, B and X. The benefits of the invention are obtainable from a surface treating agent comprising any of such single end hydrolyzable polymers.

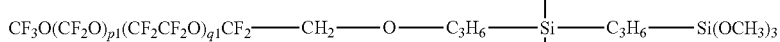
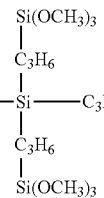

p1 + q1 = 45

-continued
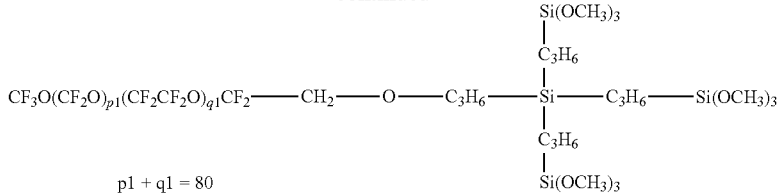
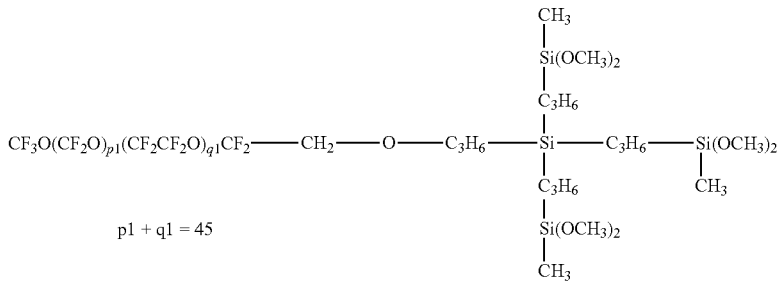
The units in parentheses may be randomly arranged.
Examples of the single end hydrolyzable polymer of formula (1) wherein Q, B, and X are other than the above-mentioned ones are shown below.
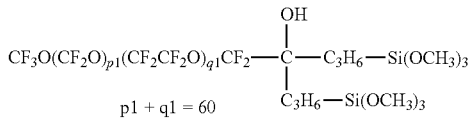
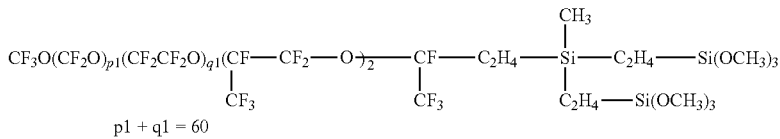
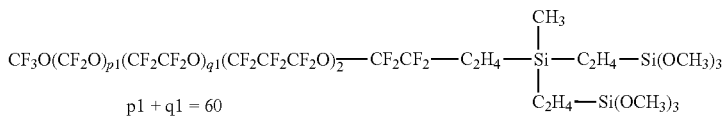
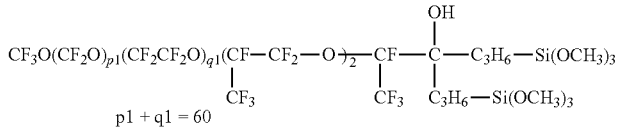
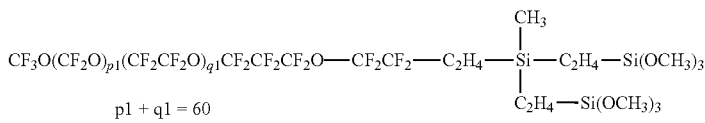

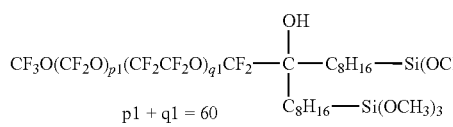
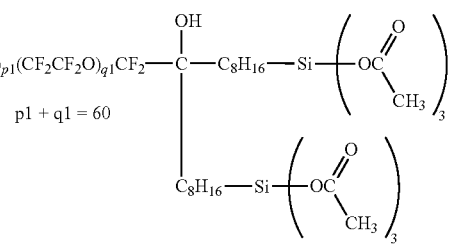

The units in parentheses may be randomly arranged.

The compound of formula (1) may be prepared by any well-known methods. For example, a single end hydrolyzable polymer of the following formula:

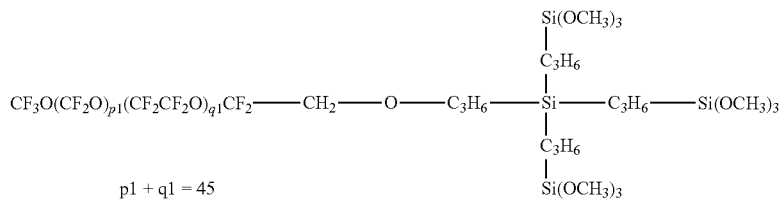

may be prepared by starting with a fluorooxyalkylene-containing polymer modified with a hydroxyl group at a single end, reacting the polymer with allyl bromide to introduce an unsaturated bond group at the end, adding chlorosilane, and effecting Grignard reaction to introduce a plurality of unsaturated bonds. This is followed by adding chlorosilane to unsaturated bond ends and subsequent alkoxy conversion or by directly adding trialkoxysilane.

may be prepared by starting with a fluorooxyalkylene-containing polymer having a carboxyl group at a single end, effecting Grignard reaction to introduce a plurality of unsaturated bonds, and adding chlorosilane to unsaturated bond ends and converting into alkoxy form, or directly adding trialkoxysilane.

Examples of the dual end hydrolyzable polymer of formula (2) include those wherein Q, B, and X are combined as shown above for the single end hydrolyzable polymer. Illustrative examples are given below.

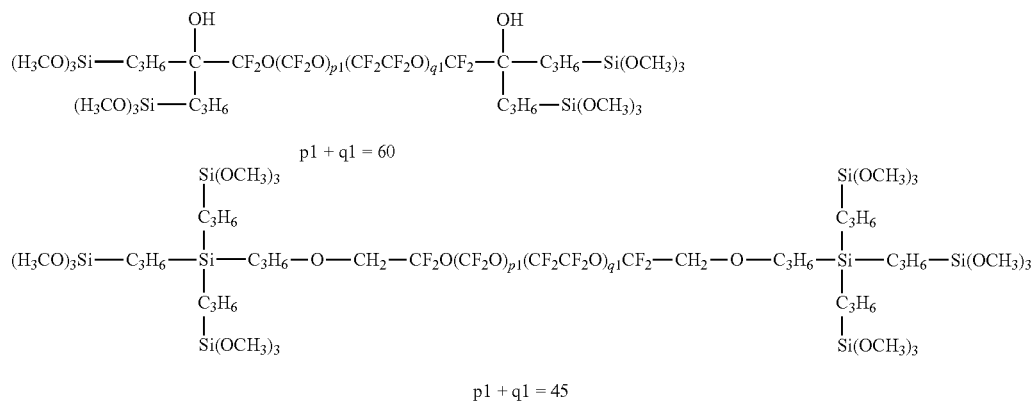

In another example, a single end hydrolyzable polymer of the following formula:

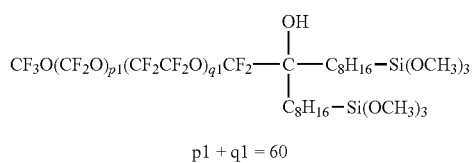

Preferred examples of the nonfunctional polymer of formula (3) include those of the general formulae (4) and (5), but are not limited thereto.

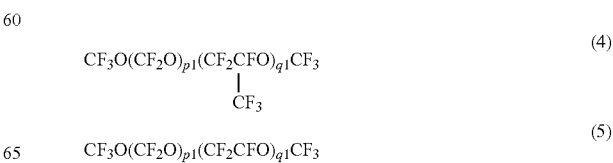

Herein p1 and q1 are such numbers that the fluorooxyalkylene-containing polymer may contain 10 to 100 repeating units.

Any commercial products may be used as the nonfunctional polymer or component (C). The polymer is commercially available under the trade name of Fomblin®, for example. Suitable polymers include the following structures.

Fomblin Y, typically Fomblin Y25 (Mw: 3,200) and Fomblin Y45 (Mw: 4,100) of the following structure are available from Solvay Solexis.

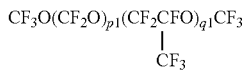

Herein p1 and q1 are such numbers as to meet the specified Mw.

Fomblin Z, typically Fomblin Z03 (Mw: 4,000), Fomblin Z15 (Mw: 8,000), and Fomblin Z25 (Mw: 9,500) of the following structure are available from Solvay Solexis.

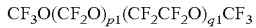

Herein p1 and q1 are such numbers as to meet the specified Mw.

As used herein, the weight average molecular weight (Mw) is determined by gel permeation chromatography (GPC) versus polystyrene standards using fluorocarbon Asahiklin AK-225 (Asahi Glass Co., Ltd.) as developing solvent.

The fluorochemical surface treating agent may comprise a partial (co)hydrolytic condensate obtained by previously subjecting the terminal hydrolyzable group of the single end hydrolyzable polymer and/or the dual end hydrolyzable polymer to partial hydrolysis and condensation in a well-known manner. It is preferred that one partial (co)hydrolytic condensate contain three or less polymer units, i.e., be trimer or lower, because a condensate of more than trimer form may be less reactive with the substrate. The condensate is present in an amount of typically up to 30%, preferably up to 20%, and more preferably up to 10% by weight, based on the weight of overall solids in the agent. Within this range, the condensate does not adversely affect solubility in the solvent and reactivity with the substrate.

In one embodiment, the fluorochemical surface treating agent comprises (A) a single end hydrolyzable polymer of formula (1) and/or a partial hydrolytic condensate thereof. In another embodiment, the surface treating agent may further comprise (B) a dual end hydrolyzable polymer of formula (2) and/or a partial hydrolytic condensate thereof. In this embodiment, the content of component (B) is up to 20 mol %, preferably up to 15 mol %, and more preferably up to 10 mol %, based on the total moles of components (A) and (B). When used, the content of component (B) is preferably at least 0.01 mol %, more preferably at least 5 mol %. As long as the content of component (B) is in the range, a film having improved chemical resistance and mar resistance is formed.

In a further embodiment, the surface treating agent may further comprise (C) a nonfunctional polymer of formula (3). In this embodiment, the content of component (C) is up to 40 mol %, preferably up to 30 mol %, and more preferably up to 20 mol %, based on the total moles of components (A), (B) and (C). When used, the content of component (C) is preferably at least 0.01 mol %, more preferably at least 5 mol %. A content of component (C) above the upper limit adversely affects chemical resistance.

To the surface treating agent, other additives may be added, if necessary, as long as the objects of the invention are not impaired. Suitable hydrolytic condensation catalysts include organotin compounds such as dibutyltin dimethoxide and dibutyltin dilaurate, organotitanium compounds such as tetra-n-butyl titanate, organic acids such as fluorinated carboxylic acids, acetic acid, and methanesulfonic acid, and inorganic acids such as hydrochloric acid and sulfuric acid. Of these, fluorinated carboxylic acids, acetic acid, tetra-n-butyl titanate, and dibutyltin dilaurate are preferred. The catalyst may be added in a catalytic amount, typically 0.01 to 5 parts, more preferably 0.1 to 1 part by weight per 100 parts by weight of components (A) to (C) combined.

The surface treating agent may be dissolved in a suitable solvent prior to coating. The solvent in which components (A) to (C) are uniformly dissolved is preferred. Suitable solvents include fluorine-modified aliphatic hydrocarbon solvents such as pentafluorobutane, perfluorohexane, perfluoroheptane, perfluorooctane, perfluorocyclohexane, and perfluoro-1,3-dimethylcyclohexane; fluorine-modified aromatic hydrocarbon solvents such as m-xylene hexafluoride, benzotrifluoride, and 1,3-trifluoromethylbenzene; fluorine-modified ether solvents such as methyl perfluoropropyl ether, methyl perfluorobutyl ether, ethyl perfluorobutyl ether, perfluoro(2-butyltetra-hydrofuran), and methoxyperfluoroheptene; fluorine-modified alkylamine solvents such as perfluorotributylamine and perfluorotripentylamine; hydrocarbon solvents such as petroleum benzine, mineral spirits, toluene, and xylene; ketone solvents such as acetone, methyl ethyl ketone, and methyl isobutyl ketone; ether solvents such as tetrahydrofuran and diethyl ether; ester solvents such as ethyl acetate; and alcohol solvents such as isopropyl alcohol. Of these, fluorine-modified solvents are desirable for solubility and wettability, with ethyl perfluorobutyl ether, decafluoropentane, pentafluorobutane, and perfluorohexane being more desirable. The solvents may be used alone or in admixture.

An optimum concentration of components (A) to (C) in the solvent is 0.01 to 50% by weight, especially 0.03 to 20% by weight, though it varies with a particular treating technique.

The surface treating agent may be applied to a substrate by any well-known techniques such as wet coating (e.g., brush coating, dipping, spraying, inkjet coating), evaporation, and sputtering. Better results are obtained when the agent is applied by spray coating, evaporation and sputtering. A coating is then cured to the substrate. The curing temperature varies with a particular curing technique. For example, the curing temperature is desirably in a range of room temperature (20° C.) to 200° C., more desirably 50 to 150° C. With respect to humidity, humid curing conditions are desirable to accelerate the reaction. The cured coating has a thickness of typically 0.1 to 100 nm, desirably 3 to 30 nm, and more desirably 5 to 15 nm although the thickness depends on the type of substrate.

The substrate to be treated with the surface treating agent is not particularly limited, and may be made of any desired materials including paper, fabric, metals, metal oxides, glass, plastics, ceramics, quartz, and sapphire glass. The surface treating agent is effective for endowing the substrate with water/oil repellency, chemical resistance, parting properties, and antifouling properties. The substrate may be pretreated on its surface, for example, by hard coat treatment or antireflective treatment. If the substrate is less adherent, adhesion may be improved by forming a SiO$_2$ layer or a layer of a silane coupling agent having hydrolyzable group or SiH group as the primer layer, or by any well-known pretreatment such as vacuum plasma treatment, atmospheric plasma treatment, alkali or acid treatment.

Since the surface treating agent contains hydrolyzable groups, desirably a silicon oxide ($SiO_2$) layer is formed on the substrate as a primer before the surface treating agent is coated thereon. Where the surface treating agent is directly bondable to substrates, typically glass substrates via hydrolyzable groups, the desired effect may be exerted without a need for $SiO_2$ layer.

Better results are obtained when glass, chemically strengthened glass, physically strengthened glass, $SiO_2$-deposited glass, sapphire glass, $SiO_2$-deposited sapphire glass, quartz substrate, and metal are used as the substrate.

Various articles may be treated with the fluorochemical surface treating agent. Preferred articles are optical articles including control panels or displays in car navigation systems, car audio systems, tablet PCs, smart phones, wearable terminals, mobile phones, digital cameras, digital video cameras, PDA, portable audio players, game consoles, LC displays in operation boards and digital signages, organic EL displays, plasma displays, touch panel displays, eyeglass lenses, camera lenses, lens filters, sunglass, medical instruments (e.g., gastroscopes), copiers, solar cell panels, protective film, and antireflective film. Among others, touch panels, antireflective film, wearable terminals, eyeglass lenses, and solar cell panels are suitable. When an article is treated with the surface treating agent, the agent forms a film which is effective for preventing fingerprints or sebum from adhering to the article and for imparting scratch resistance. The film is most useful as a water/oil repellent layer on touch panel displays.

When a substrate such as glass, sapphire glass or $SiO_2$-deposited substrate (i.e., substrate having $SiO_2$ deposited by evaporation or sputtering) is treated with the surface treating agent by spray coating, inkjet coating, spin coating, dipping, vacuum evaporation, or sputtering, there is obtained an antifoul-treated substrate which has sufficient chemical resistance and resistance to steel wool abrasion to maintain water/oil repellency over a long term.

EXAMPLE

Examples of the invention are given below by way of illustration and not by way of limitation.

Example 1

A composition #1 containing components (A) to (C), shown below, was prepared.

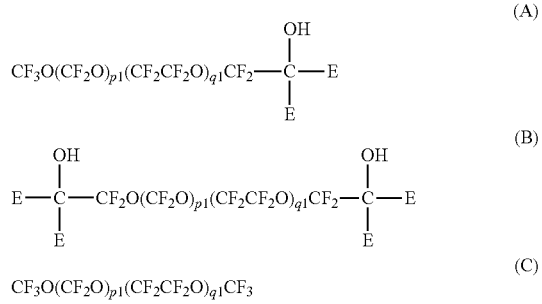

p1+q1=45, p1/q1=1.0,
E=—$C_3H_5$: —$C_3H_6$—Si($OCH_3$)$_3$=0.2:1.8,
A:B:C=92:3:5 (molar ratio)

The content (molar fraction) of each component (A, B, C) was determined by letting silica gel adsorb hydrolyzable group-containing polymers for thereby fractionating component (C), and analyzing by $^{19}$F-NMR spectroscopy.

Example 2

A composition #2 containing components (A) to (C), shown below, was prepared.

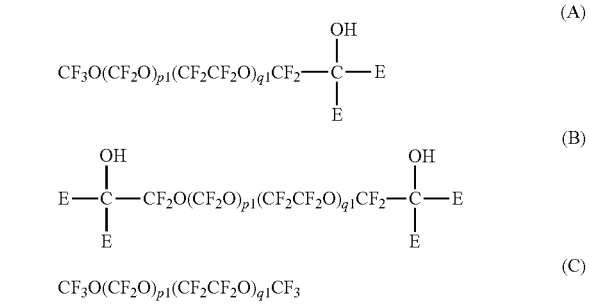

p1+q1=45, p1/q1=1.0,
E=—$C_3H_5$: —$C_3H_6$—Si($OCH_3$)$_3$=0.5:1.5,
A:B:C=90:5:5 (molar ratio)

Example 3

A composition #3 containing components (A) to (C), shown below, was prepared.

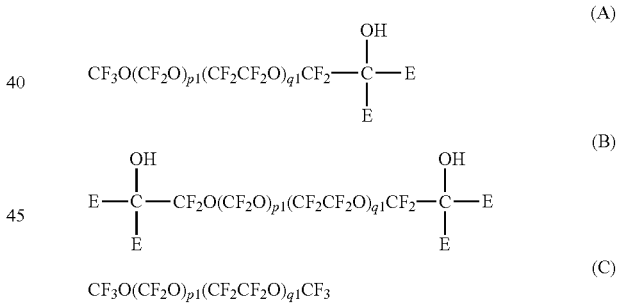

p1+q1=30, p1/q1=0.9,
E=—$C_3H_5$: —$C_3H_6$—Si($OCH_3$)$_3$=0.2:1.8,
A:B:C=85:5:10 (molar ratio)

Example 4

A composition #4 containing components (A) to (C), shown below, was prepared.

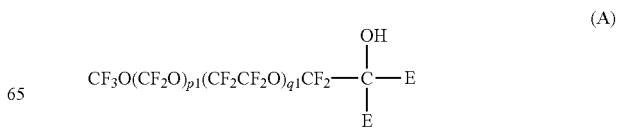

-continued

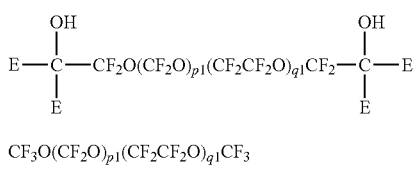
(B)

$CF_3O(CF_2O)_{p1}(CF_2CF_2O)_{q1}CF_3$
(C)

$p1+q1=80$, $p1/q1=1.1$,
$E=-C_3H_5: -C_3H_6-Si(OCH_3)_3=0.2:1.8$,
A:B:C=72:14:14 (molar ratio)

Example 5

A composition #5 containing components (A) to (C), shown below, was prepared.

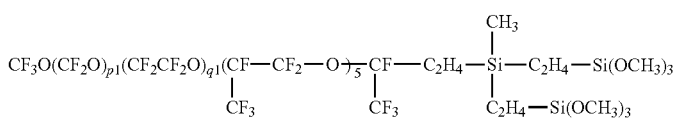

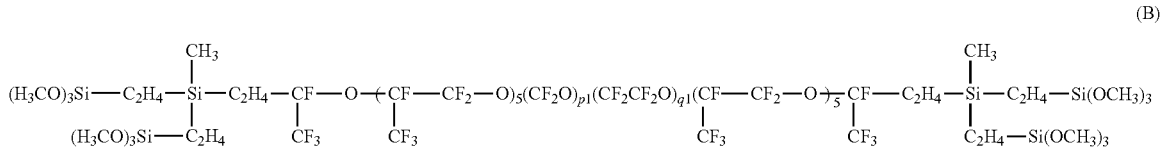

$CF_3O(CF_2O)_{p1}(CF_2CF_2O)_{q1}CF_3$
(C)

$p1+q1=45$, $p1/q1=1.0$,
A:B:C=65:12:23 (molar ratio)

Example 6

A composition #6 containing components (A) to (C), shown below, was prepared.

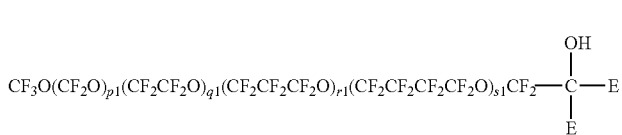

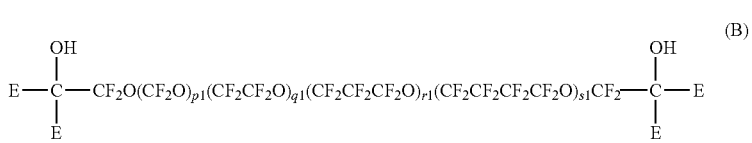

$p1+q1=45$, $p1/q1=1.1$, $r1+s1=4$, $r1/s1=0.7$,
$E=-C_3H_5: -C_3H_6-Si(OCH_3)_3=0.2:1.8$,
A:B:C=70:8:22 (molar ratio)

Example 7

A composition #7 was prepared by mixing 1 mole of composition #1 with 0.5 mole of nonfunctional perfluoropolyether FOMBLIN Z15 (Solvay Solexis, repeating units: Mw: 8,000).

Comparative Example 1

A composition #8 containing components (A) to (C), shown below, was prepared.

(A)

(B)

(C)

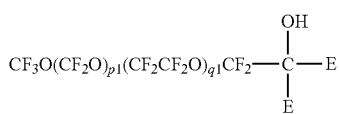
(A)

-continued

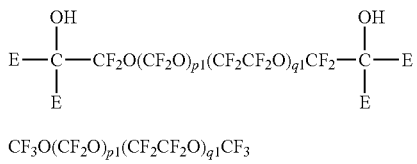
(B)

$CF_3O(CF_2O)_{p1}(CF_2CF_2O)_{q1}CF_3$
(C)

p1+q1=45, p1/q1=1.0,
E=—$C_3H_5$: —$C_3H_6$—$Si(OCH_3)_3$=1:1,
A:B:C=88:5:7 (molar ratio)

Comparative Example 2

A composition #9 containing components (A) to (C), shown below, was prepared.

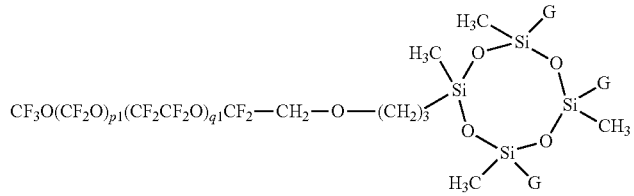
(A)

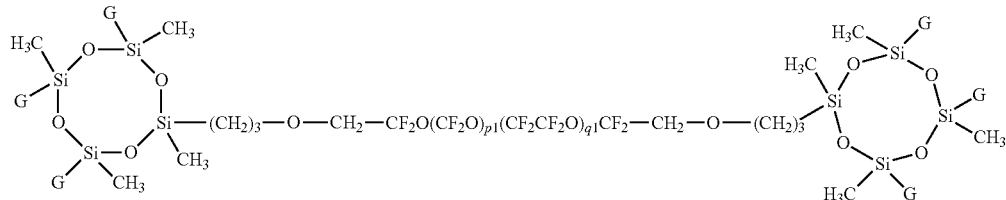
(B)

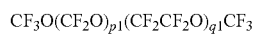
(C)

p1+q1=45, p1/q1=0.9,
E=—H: —$C_3H_6$—$Si(OCH_3)_3$=0.5:2.5,
A:B:C=90:8:2 (molar ratio)

Comparative Example 3

A composition #10 was prepared by mixing 1 mole of composition #1 with 0.95 mole of FOMBLIN Z15.

Comparative Example 4

A composition #11 containing components (A) to (C), shown below, was prepared.

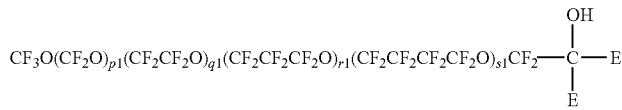
(A)

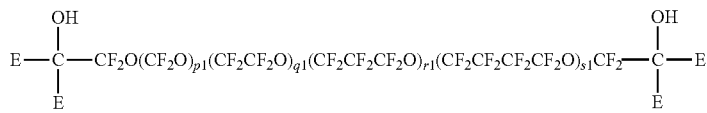
(B)

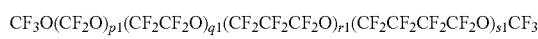
(C)

p1+q1=45, p1/q1=1.1, r1+s1=4, r1/s1=0.7,
E=—$C_3H_5$: —$C_3H_6$—Si(OCH$_3$)$_3$=0.2:1.8,
A:B:C=65:30:5 (molar ratio)

Preparation of Surface Treating Agent and Formation of Cured Film

Surface treating agents were prepared by dissolving the compositions in solvent Novec® 7200 (ethyl perfluorobutyl ether by 3M) in a concentration of 20 wt % of solids. The ratios of components in the agent are shown in Table 1.

TABLE 1

| | Composition | Component ratio (mol %) A | B | C | Rate of functionalization (b)* |
|---|---|---|---|---|---|
| Example | 1 | 92 | 3 | 5 | 1.8 |
| | 2 | 90 | 5 | 5 | 1.5 |
| | 3 | 85 | 5 | 10 | 1.8 |
| | 4 | 72 | 14 | 14 | 1.8 |
| | 5 | 65 | 12 | 23 | 2.0 |
| | 6 | 70 | 8 | 22 | 1.8 |
| | 7 | 61 | 2 | 37 | 1.8 |
| Comparative Example | 1 | 88 | 5 | 7 | 1.0 |
| | 2 | 90 | 8 | 2 | 2.5 |
| | 3 | 47 | 2 | 51 | 1.8 |
| | 4 | 65 | 30 | 5 | 1.8 |

*Rate of functionalization (b) corresponds to an average of b in formulae (1) and (2).

Onto glass having SiO$_2$ of 10 nm evaporated on its outermost surface (Gorilla® 2 by Corning, 50 mm×100 mm), each surface treating agent was deposited by vacuum evaporation under the following conditions. The deposit was held at 80° C. in an atmosphere of humidity 80% for 1 hour, obtaining a cured film.

Apparatus and Conditions of Vacuum Evaporation
  Apparatus: compact vacuum evaporation unit VPC-250F (ULVAC KIKO Inc.)
  Pressure: $2.0 \times 10^{-3}$ Pa to $3.0 \times 10^{-2}$ Pa
  Temperature (ultimate temperature of boat): 500° C.
  Distance: 20 mm
  Charge of agent: 10 mg
  Amount evaporated: 10 mg The cured film was evaluated for water repellency, coefficient of dynamic friction, chemical resistance and abrasion resistance by the following tests. The tests were conducted at a temperature of 25° C. and a humidity of 50%. The results are shown in Table 2.

Water Repellency

Using a contact angle meter Drop Master (Kyowa Interface Science Co., Ltd.), the cured film on glass was measured for a contact angle with water (2 μl droplet) as an index of water repellency.

Coefficient of Dynamic Friction

Using a surface tester 14 FW (Shinto Scientific Co., Ltd.), the cured film was measured for a coefficient of dynamic friction by rubbing with fabric under the following conditions.
  Fabric: Bemcot (Asahi Kasei Fibers Corp.)
  Contact area: 10 mm×35 mm
  Load: 100 g Chemical Resistance A chemical resistance test was conducted to determine an index of adhesion. The cured film was immersed in 1 wt % NaOH aqueous solution for 72 hours before a contact angle with water was measured as above.

Abrasion Resistance

Using an abrasion tester TriboGear Type 30S (Shinto Scientific Co., Ltd.), the cured film was rubbed with steel wool. After 10,000 back-and-forth strokes of rubbing, a contact angle with water was measured as above.
  Steel wool: #0000
  Contact area: 1 cm$^2$
  Load: 1 kg

TABLE 2

| | | Contact angle with water (°) | coefficient of dynamic friction | Contact angle with water (°) after chemical test | Contact angle with water (°) after abrasion test |
|---|---|---|---|---|---|
| Example | 1 | 116 | 0.02 | 110 | 110 |
| | 2 | 115 | 0.02 | 105 | 110 |
| | 3 | 116 | 0.02 | 109 | 111 |
| | 4 | 115 | 0.03 | 111 | 105 |
| | 5 | 115 | 0.03 | 107 | 105 |
| | 6 | 115 | 0.02 | 107 | 108 |
| | 7 | 115 | 0.02 | 105 | 110 |
| Comparative Example | 1 | 115 | 0.02 | 97 | 110 |
| | 2 | 115 | 0.03 | 110 | 85 |
| | 3 | 116 | 0.02 | 95 | 110 |
| | 4 | 114 | 0.03 | 111 | 98 |

It is evident from the test results that Comparative Example 1 exhibits poor adhesion to the substrate and less chemical resistance due to a low rate of functionalization. Comparative Example 2 is adherent to the substrate, but exhibits poor resistance to steel wool abrasion due to a bulky linking group. Comparative Example 3 exhibits poor adhesion to the substrate and less chemical resistance due to an excessive content of nonfunctional polymer or component (C). Comparative Example 4 exhibits poor resistance to steel wool abrasion due to a higher content of dual end hydrolyzable polymer or component (B).

In contrast, both chemical resistance and abrasion resistance are met by Examples in which the content of component (B) is 0.1 to 20 mol % based on the total moles of components (A) and (B) and the content of component (C) is 0.1 to 40 mol % based on the total moles of components (A), (B) and (C).

The fluorochemical surface treating agent cures into a film having improved water/oil repellency. The agent is quite effective in such applications as touch panel displays and antireflective film where it is important to keep visibility despite a probability of oil and fat sticking. Fulfilling both chemical resistance and abrasion resistance, the film maintains a satisfactory antifouling surface over a long term even when stains are kept stuck for a long time or under the situation where daily items such as fabrics and keys frequently come in contact with the film.

Japanese Patent Application No. 2014-161004 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A fluorochemical surface treating agent, comprising:
    (A) a hydrolyzable group-containing silane modified with a fluorooxyalkylene-containing polymer, represented by the average compositional formula (1) and/or a partial hydrolytic condensate thereof,

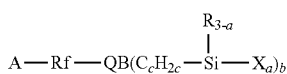

(1)

wherein A is a monovalent fluorinated group terminated with —CF$_3$,

Rf is —(CF$_2$)$_d$—(OCF$_2$)$_p$(OCF$_2$CF$_2$)$_q$(OCF$_2$CF$_2$CF$_2$)$_r$(OCF$_2$CF$_2$CF$_2$CF$_2$)$_s$(OCF(CF$_3$)CF$_2$)$_t$—O(CF$_2$)$_d$—, d is independently an integer of 0 to 5, p, q, r, s and t are each independently an integer of 0 to 200, p+q+r+s+t is 10 to 200, units in parentheses may be randomly arranged, Q is a single bond or a divalent organic group, B is a divalent group: -J$_2$C—, a divalent group: -L$_2$Si—, a trivalent group: -JC≡, a trivalent group: -LSi≡, a tetravalent group: —C≡, or a tetravalent group: —Si≡, wherein J is independently an alkyl group, hydroxyl group, —C$_3$H$_5$, or silyl ether group: K$_3$SiO—, K is independently hydrogen, alkyl, aryl or alkoxy, L is independently alkyl, alkoxy or chloro, R is a monovalent organic group, and X is a hydrolyzable group, a is an integer of 1 to 3, b is an integer of 1 to 3, an average of b being 1.5 to 3.0, c is an integer of 1 to 10; and (B) a hydrolyzable group-containing silane modified with a fluorooxyalkylene-containing polymer, represented by the average compositional formula (2) and/or a partial hydrolytic condensate thereof, component (B) being present in an amount of 0.1 to 20 mol % based on the total moles of components (A) and (B),

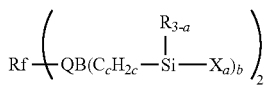

(2)

wherein Rf, Q, B, R, X, a, b, and c are as defined in formula (1).

2. The fluorochemical surface treating agent of claim 1, further comprising (C) a fluorooxyalkylene-containing polymer having the general formula (3), component (C) being present in an amount of 0.1 to 40 mol % based on the total moles of components (A), (B) and (C), D-Rf-D (3)

wherein Rf is as defined in formula (1) and D is independently fluorine, hydrogen, or a monovalent fluorinated group terminated with —CF$_3$, —CF$_2$H or —CFH$_2$.

3. An article treated with the fluorochemical surface treating agent of claim 2.

4. An optical article treated with the fluorochemical surface treating agent of claim 2.

5. A glass, chemically strengthened glass, physically strengthened glass, SiO$_2$-deposited glass, sapphire glass, SiO$_2$-deposited sapphire glass, quartz substrate, or metal treated with the fluorochemical surface treating agent of claim 2.

6. A touch panel, antireflective film, wearable terminal, eyeglass lens, or solar cell panel treated with the fluorochemical surface treating agent of claim 2.

7. The fluorochemical surface treating agent of claim 1, wherein Q is a single bond or a substituted or unsubstituted, divalent hydrocarbon group of 2 to 12 carbon atoms which may contain at least one structure selected from an amide bond, ether bond, ester bond, diorganosilylene group, and —Si[OH][(CH$_2$)$_g$Si(CH$_3$)$_3$]— wherein g is an integer of 2 to 4.

8. An article treated with the fluorochemical surface treating agent of claim 7.

9. An optical article treated with the fluorochemical surface treating agent of claim 7.

10. A glass, chemically strengthened glass, physically strengthened glass, SiO$_2$-deposited glass, sapphire glass, SiO$_2$-deposited sapphire glass, quartz substrate, or metal treated with the fluorochemical surface treating agent of claim 7.

11. A touch panel, antireflective film, wearable terminal, eyeglass lens, or solar cell panel treated with the fluorochemical surface treating agent of claim 7.

12. The fluorochemical surface treating agent of claim 1, wherein X is a hydrolyzable group selected from the group consisting of C$_1$-C$_{10}$ alkoxy groups, C$_2$-C$_{10}$ alkoxyalkoxy groups, C$_1$-C$_{10}$ acyloxy groups, C$_2$-C$_{10}$ alkenyloxy groups, halogen groups, and silazane groups.

13. The fluorochemical surface treating agent of claim 1, which is diluted with a solvent.

14. The fluorochemical surface treating agent of claim 13, wherein the solvent is selected from the group consisting of methyl perfluorobutyl ether, ethyl perfluorobutyl ether, methoxyperfluoroheptene, decafluoropentane, pentafluorobutane, and perfluorohexane.

15. An article treated with the fluorochemical surface treating agent of claim 1.

16. An optical article treated with the fluorochemical surface treating agent of claim 1.

17. A glass, chemically strengthened glass, physically strengthened glass, SiO$_2$-deposited glass, sapphire glass, SiO$_2$-deposited sapphire glass, quartz substrate, or metal treated with the fluorochemical surface treating agent of claim 1.

18. A touch panel, antireflective film, wearable terminal, eyeglass lens, or solar cell panel treated with the fluorochemical surface treating agent of claim 1.

* * * * *